(12) United States Patent
Kameishi et al.

(10) Patent No.: US 10,624,606 B2
(45) Date of Patent: Apr. 21, 2020

(54) ULTRASOUND DIAGNOSTIC APPARATUS

(71) Applicant: TOSHIBA MEDICAL SYSTEMS CORPORATION, Otawara-shi (JP)

(72) Inventors: Wataru Kameishi, Nasushiobara (JP); Hiroyuki Shibanuma, Yaita (JP); Satoshi Kamiyama, Otawara (JP); Masaaki Ishitsuka, Nasushiobara (JP); Tomohiro Fujita, Nasushiobara (JP); Teruki Hagihara, Nasushiobara (JP); Shuta Fujiwara, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 1039 days.

(21) Appl. No.: 14/976,821

(22) Filed: Dec. 21, 2015

(65) Prior Publication Data

US 2016/0183917 A1 Jun. 30, 2016

(30) Foreign Application Priority Data

Dec. 24, 2014 (JP) ................................. 2014-260011

(51) Int. Cl.
*A61B 8/00* (2006.01)
*G01S 7/52* (2006.01)
(Continued)

(52) U.S. Cl.
CPC .............. *A61B 8/4483* (2013.01); *A61B 8/54* (2013.01); *B06B 1/0215* (2013.01);
(Continued)

(58) Field of Classification Search
CPC ....... A61B 8/4483; A61B 8/54; B06B 1/0215; B06B 2201/76; G01S 15/8915; G01S 7/5202; G01S 7/52042; G01S 7/52077
See application file for complete search history.

(56) References Cited

U.S. PATENT DOCUMENTS 4,943,783 A * 7/1990 Nojima ................. H03F 1/3229
330/149
2014/0249420 A1* 9/2014 Akahane ................. A61B 8/54
600/459

FOREIGN PATENT DOCUMENTS

JP 52-34779 A 3/1977
JP 61043810 A * 3/1986
(Continued)

OTHER PUBLICATIONS

Machine Translation for JP 61-043810 (Nishi); obtained on Sep. 6, 2019 (Year: 1986).*

*Primary Examiner* — Christopher L Cook
(74) *Attorney, Agent, or Firm* — Oblon, McClelland, Maier & Neustadt, L.L.P.

(57) ABSTRACT

An ultrasound diagnostic apparatus according to a present embodiment includes driving pulse generating circuitries and a transmission control circuitry. The transmission control circuitry turns on a switching element of respective driving pulse generating circuitries of the driving pulse generating circuitries to be grounded, and thereby controls so as to make an output impedance of the respective driving pulse generating circuitries become a low impedance. The transmission control circuitry turns off the switching element of the respective driving pulse generating circuitries, and thereby controls so as to make the output impedance become a high impedance by means of a resistance value of the resistance. The transmission control circuitry controls so as to make the output impedance of the respective driving pulse generating circuitries become a lower impedance during a transmission period in which the ultrasound is transmitted than during a reception period in which a reflected wave of the ultrasound is received.

9 Claims, 9 Drawing Sheets

(51) Int. Cl.
*B06B 1/02* (2006.01)
*G01S 15/89* (2006.01)

(52) U.S. Cl.
CPC ........ *G01S 7/5202* (2013.01); *G01S 7/52077* (2013.01); *B06B 2201/76* (2013.01); *G01S 7/52042* (2013.01); *G01S 15/8915* (2013.01)

(56) References Cited

FOREIGN PATENT DOCUMENTS

| | | |
|---|---|---|
| JP | 63-145957 | 6/1988 |
| JP | 2012-200460 | 10/2012 |
| JP | 2013-52154 | 3/2013 |
| JP | 2014-124427 | 7/2014 |

\* cited by examiner

ULTRASOUND DIAGNOSTIC APPARATUS

CROSS-REFERENCE TO RELATED APPLICATION

This application is based upon and claims the benefit of priority from Japanese Patent Application No. 2014-260011, filed on Dec. 24, 2014, the entire contents of which are incorporated herein by reference.

FIELD

An embodiment as one aspect of the present invention relates to an ultrasound diagnostic apparatus.

BACKGROUND

In the medical field, ultrasound diagnostic apparatuses are utilized for various kinds of diagnosis and treatment because they can be used to noninvasively examine the internal structure or blood flow state of a patient. When using an ultrasound diagnostic apparatus, the operator brings an ultrasound probe that includes transducers (piezoelectric transducers) at a distal end thereof into contact with the body surface of a subject and transmits ultrasound into the body of the subject, and then receives reflected waves that arise due to a mismatch of acoustic impedances inside the subject with the transducers of the ultrasound probe. An ultrasound image is generated based on reception signals that are obtained in this manner.

In recent years, a technique referred to as "harmonic imaging" is being developed that utilizes nonlinear components that are detected in very small amounts during propagation of an acoustic wave. The velocity of an ultrasound wave that propagates through a substance has a property such that a portion in which the sound pressure is high travels faster and a portion in which the sound pressure is low travels slower. Therefore, even when the transmitted ultrasound is a sinusoidal wave consisting of fundamental wave components, distortion gradually arises during the course of propagation, and consequently a higher harmonic wave having nonlinear components becomes included therein. Harmonic imaging that utilizes such kind of higher harmonic components are broadly divided into tissue harmonic imaging (THI) and contrast harmonic imaging (CHI) depending on the kind of signal that is visualized. THI is used for imaging higher harmonic components generated from tissue when ultrasound propagates through the tissue. CHI is used for imaging higher harmonic components generated when a contrast agent including microbubbles (bubbles) for ultrasound is administered to a subject and the bubbles resonate and disintegrate.

In harmonic imaging, fundamental wave components and higher harmonic components are separated by filtering or waveform calculation to extract the higher harmonic components. For example, in a technique referred to as "amplitude modulation", the ultrasound that is transmitted is transmitted three times so that the relative sound pressures thereof are ½, 1, and ½, and by subtracting the total of two reception signals in which the transmission sound pressure is ½ from a reception signal in which the transmission sound pressure is 1, the fundamental wave components can be removed and the higher harmonic components can be extracted. Various techniques other than amplitude modulation are also being developed, such as a phase inversion technique and a technique that combines amplitude modulation and phase inversion.

As described above, in harmonic imaging, plural sets of transmission and reception may be performed to extract higher harmonic components, the plural sets being performed in different sound pressures. A method is also used that sets a voltage applied to the transducers to different values to set the transmission sound pressure to different values of 1 and ½. However, it is difficult to set an applied voltage to different values with high accuracy. Therefore, the sound pressure is adjusted by actuating all of the transducers when the transmission sound pressure is 1, and actuating half of the transducers when the transmission sound pressure is ½. In the case of setting the transmission sound pressure to ½, in order to match the transmission aperture with the transmission aperture in a case where the transmission sound pressure is 1, control is performed so as to actuate odd-numbered or even-numbered transducers (that is, every second channel).

However, there has been the problem that, due to crosstalk, that is, leaking in of transmission signals from channels for which transducer are driven, transmission pulses are generated even from channels that are not transmitting, that is, channels in which a transducer is not driven. In some cases, due to transmission from channels that are not transmitting, the relative sound pressure that is actually transmitted to a subject exceeds ½. Accordingly, fundamental wave components cannot be cancelled out by the aforementioned amplitude modulation technique or phase inversion technique, and tissue or bubble components linger and cause a decrease in the S/N ratio or a deterioration in the image quality.

Therefore, an ultrasound diagnostic apparatus has been proposed in which crosstalk is avoided by performing transmission at a low voltage from channels that are not transmitting. According to a related art, because a previously set transmission pulse is transmitted from channels that are not transmitting, a fundamental waveform is cancelled by subsequently subtracting those components.

Instead of the above described technology, an ultrasound diagnostic apparatus is desired that enables more accurate transmission sound pressure control by ensuring transmission pulses are not generated due to crosstalk in channels that are not transmitting.

BRIEF DESCRIPTION OF THE DRAWINGS

In accompanying drawings.

DETAILED DESCRIPTION

Hereunder, an embodiment of an ultrasound diagnostic apparatus will be described with reference to the accompanying drawings.

To solve the above-described problems, the present embodiment provides the ultrasound diagnostic apparatus that controls transducers each corresponding to a channel of channels that are independent to cause the transducers to transmit and receive ultrasound, including driving pulse generating circuitries and a transmission control circuitry. The driving pulse generating circuitries are each corresponding to the channel, each of the driving pulse generating circuitries including a switching element in which one end side of two ends is grounded and a resistance in which the other end side of the switching element is connected in series with respective transducers of the transducers, and the each of the driving pulse generating circuitries being configures to apply a driving pulse to the respective transducers. The transmission control circuitry is configured to separately control each of a transmitting channel of the channels and a non-transmitting channel of the channels, the transmitting channel transmitting the ultrasound, and the non-transmitting channel not transmitting the ultrasound. The transmission control circuitry is configured to: turn on a switching element of respective driving pulse generating circuitries of the driving pulse generating circuitries to be grounded, and thereby control so as to make an output impedance of the respective driving pulse generating circuitries become a low impedance; turn off the switching element of the respective driving pulse generating circuitries, and thereby control so as to make the output impedance become a high impedance by means of a resistance value of the resistance; and control so as to make the output impedance of the respective driving pulse generating circuitries become a lower impedance during a transmission period in which the ultrasound is transmitted than during a reception period in which a reflected wave of the ultrasound is received.

1. Configuration

Figure 1:
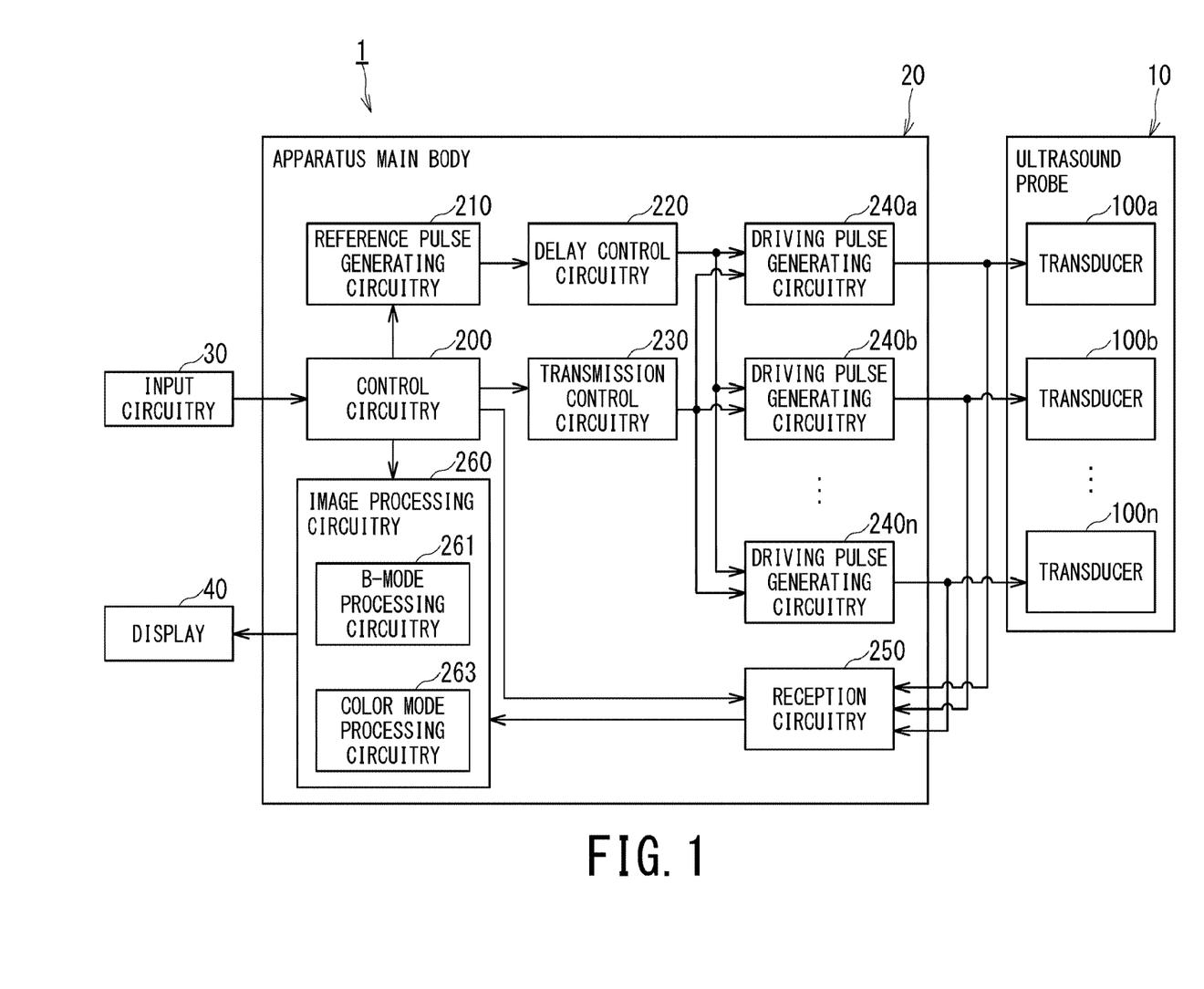
FIG. 1 is a conceptual configuration diagram illustrating an example of an ultrasound diagnostic apparatus according to a present embodiment.

FIG. 1 is a conceptual configuration diagram illustrating an example of an ultrasound diagnostic apparatus according to a present embodiment.

FIG. 1 illustrates an ultrasound diagnostic apparatus 1 according to the present embodiment. The ultrasound diagnostic apparatus 1 includes an ultrasound probe 10, an apparatus main body 20, an input circuitry 30 and a display 40. Note that in some cases the apparatus main body 20, the input circuitry 30 and the display 40 are referred to as "ultrasound diagnostic apparatus", and in such cases the ultrasound diagnostic apparatus is connected to an ultrasound probe that is provided outside of the ultrasound diagnostic apparatus.

Ultrasound probes that support sector scanning, linear scanning or convex scanning or the like are available as the ultrasound probe 10, one of which is freely selected according to the site to be diagnosed. The ultrasound probe 10 is connected by a cable or the like to the apparatus main body 20, and transducers 100 are one-dimensionally arranged at a distal end of the ultrasound probe 10, the number of the transducers 100 being N (100a, 100b . . . 100n). Each transducer 100 of the ultrasound probe 10 has a function that converts an electrical pulse applied from the apparatus main body 20 to an ultrasound pulse and transmits the ultrasound pulse into the subject, and on the other hand, receives an ultrasound echo generated inside the subject and outputs the ultrasound echo as a reception signal that is an electrical signal to the apparatus main body 20. The ultrasound probe 10 forms an ultrasound transmission beam by means of ultrasound pulses that are transmitted from the respective transducers 100.

Note that the transducers 100 are not limited to a one-dimensional array, and a three-dimensional stereoscopic image can be acquired in real-time by disposing the transducers 100 in a two-dimensional array shape. In the case of obtaining a three-dimensional stereoscopic image, a probe for 3D scanning is provided as the ultrasound probe 10. A two-dimensional array probe or a mechanical four-dimensional probe may be mentioned as examples of a probe for three-dimensional scanning.

The input circuitry 30 is a circuitry into which a signal is input from an input device such as a pointing device (a mouse or the like) or a keyboard or the like that can be operated by an operator. Here, it is assumed that the input device itself is also included in the input circuitry 30. When the input device is operated by the operator, the input circuitry 30 generates an input signal in accordance with the operation and outputs the input signal to a control circuitry 200. The apparatus main body 20 may also be connected via a network to the other image diagnosis apparatus (modality) as well as an image server such as a DICOM (Digital Imaging and Communications in Medicine) server or an image processing apparatus.

The display 40 is constituted by a general display output apparatus such as a liquid crystal display or an OLED (organic light emitting diode) display. The display 40 displays a generated ultrasound image or the like on the display in accordance with control of the control circuitry 200.

The apparatus main body 20 includes the control circuitry 200, a reference pulse generating circuitry 210, a delay control circuitry 220, a transmission control circuitry 230, a driving pulse generating circuitry 240, a reception circuitry 250 and an image processing circuitry 260. As shown in FIG. 1, the number of the driving pulse generating circuitries 240 is N (240a, 240b . . . 240n) provided in correspondence with the number of the transducers 100.

Note that, digital circuitries constituting the reference pulse generating circuitry 210, the delay control circuitry 220, the transmission control circuitry 230, the driving pulse generating circuitry 240 and the reception circuitry 250 may be disposed in the ultrasound probe 10 instead of the apparatus main body 20. Further, the reference pulse generating circuitry 210, the delay control circuitry 220, the transmission control circuitry 230, the driving pulse generating circuitry 240 and the reception circuitry 250 can also be realized by software that causes a processor to execute a program that is stored in a predetermined memory.

The control circuitry 200 includes processing circuitry and a memory circuitry (for example, a memory) or the like, and carries out unified control of the respective portions of the ultrasound diagnostic apparatus 1.

The term "processing circuitry" refers to, in addition to a dedicated or general-purpose CPU (central processing unit) or MPU (microprocessor unit), an application specific integrated circuit (ASIC) and a programmable logic device or the like. A simple programmable logic device (SPLD), a complex programmable logic device (CPLD) and a field programmable gate array (FPGA) may be mentioned as examples of the programmable logic device. The processing circuitry reads out and executes a program that is stored in a memory or is directly incorporated into the processing circuitry.

The processing circuitry may be constituted by a single circuitry, or may be constituted by combining independent circuitries. In the latter case, a memory may be individually provided for each circuitry of the circuitries, or a program corresponding to the functions of the circuitries may be stored in a single memory.

The reference pulse generating circuitry 210 generates a reference pulse in accordance with a control signal from the control circuitry 200.

The delay control circuitry 220 delays a reference pulse based on a delay time for converging transmission ultrasound at a predetermined depth for obtaining a narrow beam width during transmission, and a delay time for emitting transmission ultrasound in a predetermined direction, and supplies the reference pulse to the driving pulse generating circuitry 240.

The transmission control circuitry 230 controls the driving pulse generating circuitry 240 by means of a control signal for forming driving pulses and a control signal for distinguishing between a transmission period and a reception period. The driving pulse generating circuitry 240 generates a driving pulse for forming transmission pulses from the respective transducers 100 based on a combination of the control signals. Further, by using a combination of these control signals, the driving pulse generating circuitry 240 selects transducers 100 which are to transmit a transmission pulse and transducers 100 which are not to transmit a transmission pulse from among the transducers 100. Selection of the transducers 100 which are to transmit a transmission pulse and the transducers 100 which are not to transmit a transmission pulse is performed to control the transmission sound pressure. For example, In a case in which transmission is to be performed using a certain predetermined number of transducers at the time of transmission the sound pressure is taken as a value of "1", and when transmitting a transmission sound pressure so that the sound pressure becomes a value of "½" relative to the value "1", odd-numbered or even-numbered transducers 100 are allocated as the transmitting transducers 100 or as the non-transmitting transducers 100. Note that, during reception, receiving is performed using both the transmitting transducers 100 and the non-transmitting transducers 100.

The driving pulse generating circuitry 240 generates a driving pulse for transmitting ultrasound, and applies the generated driving pulse to a corresponding transducer 100. The driving pulse generating circuitry 240 is provided for each transducer 100, respectively, and generates a driving pulse based on a delayed reference pulse. Hereunder, the transducer 100 that transmits a transmission pulse and the driving pulse generating circuitry 240 corresponding to the relevant transducer 100 are referred to in combination as a "channel". Further, a channel that performs transmission is referred to as a "transmitting channel" and a channel that is not transmitting is referred to as a "non-transmitting channel".

The driving pulse is an electrical pulse that is applied to the transducer 100, and is a bipolar pulse signal that corresponds to a waveform to be transmitted from the transducer 100. The sound pressure of ultrasound that is transmitted is determined according to the voltage of the driving pulse. Further, the frequency of the ultrasound and the number of ultrasound bursts are determined according to the burst frequency and number of bursts of the driving pulses.

The driving pulse generating circuitries 240 of the respective channels that are allocated as transmitting channels by control of the transmission control circuitry 230 generate driving pulses with a waveform in which the polarities or the voltages that drive the transducers 100 differ in accordance with pulses supplied from the reference pulse generating circuitry 210. In contrast, channels that are allocated as non-transmitting channels do not generate a driving pulse. Further, based on a control signal from the transmission control circuitry 230, the impedance (hereunder, referred to as "output impedance") of the driving pulse generating circuitry 240 of a non-transmitting channel as seen from the transducer 100 side is set to a low impedance during a transmission period of the transmitting channels. That is, during a transmission period in which ultrasound is transmitted into a subject from the transducers 100, the output impedance of the driving pulse generating circuitry 240 as seen from the transducer 100 side is set to an impedance that is lower than during a reception period in which a reflected wave that is generated inside the subject is received by the transducer 100. On the other hand, during the reception period the output impedance of the driving pulse generating circuitries 240 of all the channels is set to a high impedance, irrespective of whether a channel is a transmitting channel or a non-transmitting channel. Control of the output impedance in the driving pulse generating circuitry 240 is described later.

The reception circuitry 250 performs A/D conversion of reception signals that are received with the transducers 100, and forms a reception beam based on the converted digital data. An ultrasound image is generated based on the reception beam.

The image processing circuitry 260 includes a B-mode processing circuitry 261 and a color mode processing circuitry 263, and generates an ultrasound image of B-mode data, color Doppler data and a Doppler spectrum or the like based on the obtained reception beam. The image processing circuitry 260 generates a B-mode image and a color Doppler image as ultrasound images by causing the B-mode data and color Doppler data to correspond in the scanning direction and storing the resulting data, and also generates a Doppler spectrum image and an M-mode image as ultrasound images by time-sequentially storing a Doppler spectrum and B-mode data that are obtained with respect to a predetermined scanning direction.

Figure 2A:
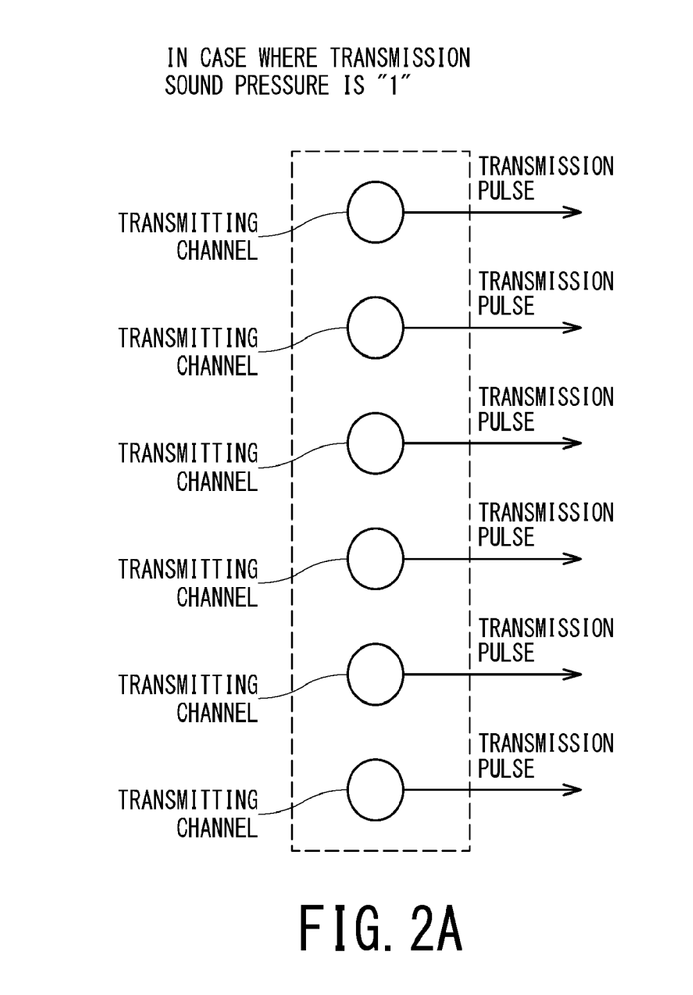
FIGS. 2A and 2B are diagrams for describing transmitting channels and non-transmitting channels.
Figure 2B:
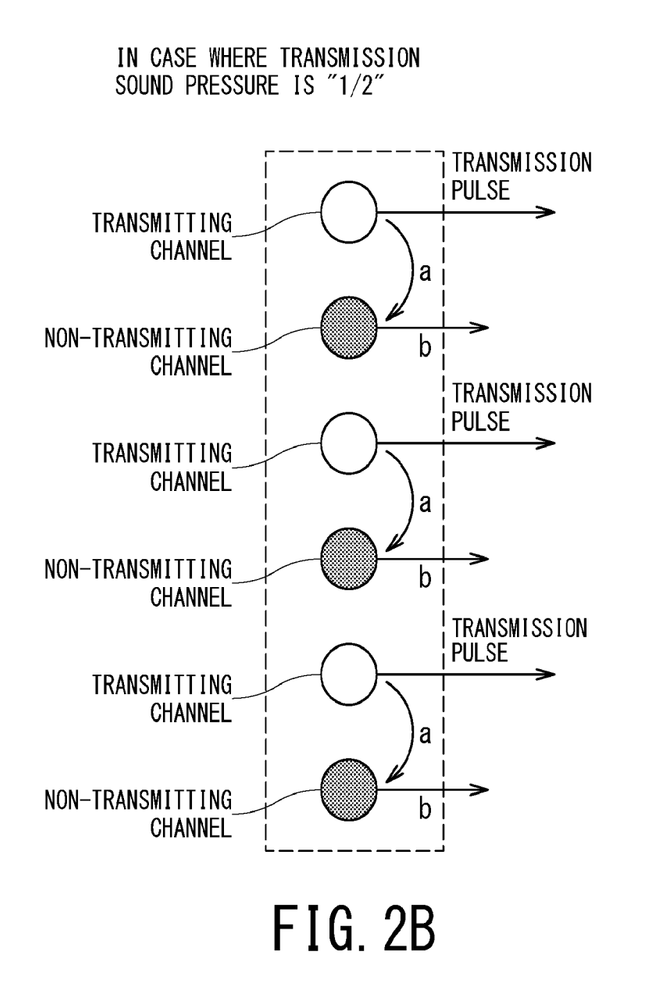

FIGS. 2A and 2B are diagrams for describing the transmitting channels and the non-transmitting channels.

In harmonic imaging, the transmission sound pressure is changed by controlling the number of channels that transmit. For example, FIG. 2A illustrates a case where the transmission sound pressure is "1", and FIG. 2B illustrates a case where the transmission sound pressure is "½". To facilitate the description, six channels are illustrated in FIGS. 2A and 2B, although in practice the number of channels is much greater, and for example is 128 channels.

As shown in FIG. 2A, in a case where the transmission sound pressure is "1", all the channels are allocated as transmitting channels and a transmission pulse is transmitted from all the channels.

In contrast, as shown in FIG. 2B, in a case where the transmission sound pressure is "½", for example, odd-numbered channels are allocated as transmitting channels, and even-numbered channels are allocated as non-transmitting channels. The allocation of the odd-numbered channels and even-numbered channels as transmitting/non-transmitting channels is interchanged for each transmission operation. A transmission pulse is transmitted from the transmitting channels.

In FIG. 2B, as shown by the respective arrows a, the non-transmitting channels receive the influence of crosstalk, that is, leaking in of a transmission signal from a transmitting channel. When a channel is allocated as a non-transmitting channel, a driving pulse is not generated for that channel and a transmission pulse is not formed. Nevertheless, a voltage is applied to the relevant transducer 100 by the crosstalk from a channel that transmits and, as shown by the respective arrows b, a transmission pulse is generated. In some cases the transmission sound pressure that is actually output becomes greater than ½ due to the influence of crosstalk from such transmitting channels on the non-transmitting channels.

Note that, to simplify the description, in FIGS. 2A and 2B examples are shown in which all the channels that exist in the probe are split into odd-numbered channels and even-numbered channels that perform transmission in an alternating manner. However, in an actual probe the number of transducers to be used is sometimes determined according to the aperture width, and transducers 100 that are not utilized depending on the aperture width are also present as non-transmitting channels. Therefore, crosstalk also occurs at transducers 100 that are not selected to form an aperture. Further, although the number of transducers to be used is determined in accordance with the aperture width, the positions of the transducers 100 to be used for each transmission are changed so that an imbalance does not arise with respect to the transducers 100 that are used. For example, control is performed so as to use some transducers 100 while shifting the positions thereof by an amount corresponding to a predetermined number of transducers for each pulse, and at the start the transducers 100 that have not been selected in an aperture range are used in sequence.

In the ultrasound diagnostic apparatus 1 according to the present embodiment, as described above, a voltage that is generated by crosstalk in non-transmitting channels is reduced by controlling the output impedance of the driving pulse generating circuitries 240 that are not used for transmission.

2. Operation

Figure 3:
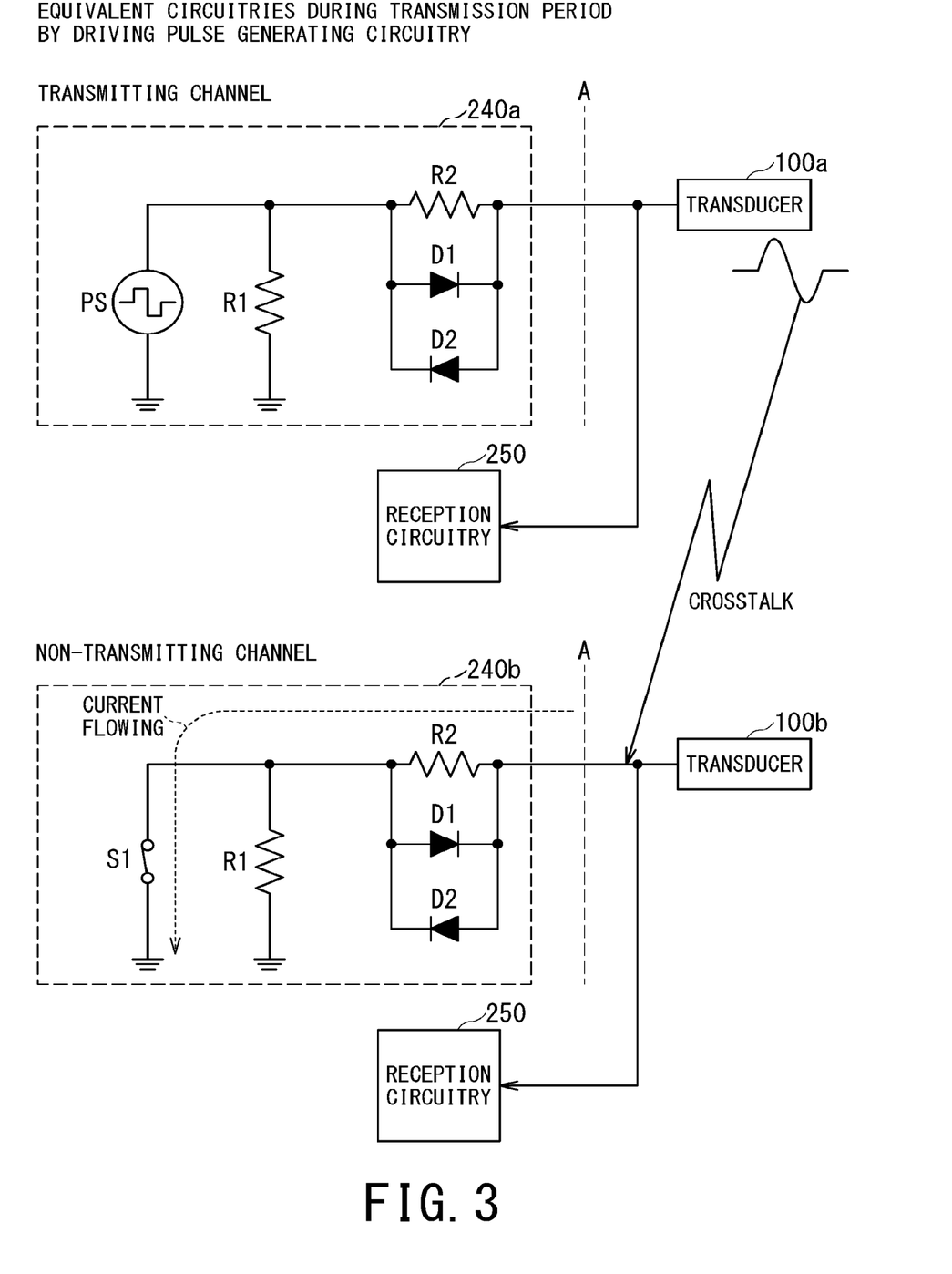
FIG. 3 is a diagram for describing equivalent circuitries during a transmission period, the equivalent circuitries being included in the driving pulse generating circuitry of the ultrasound diagnostic apparatus according to the present embodiment.
Figure 4:
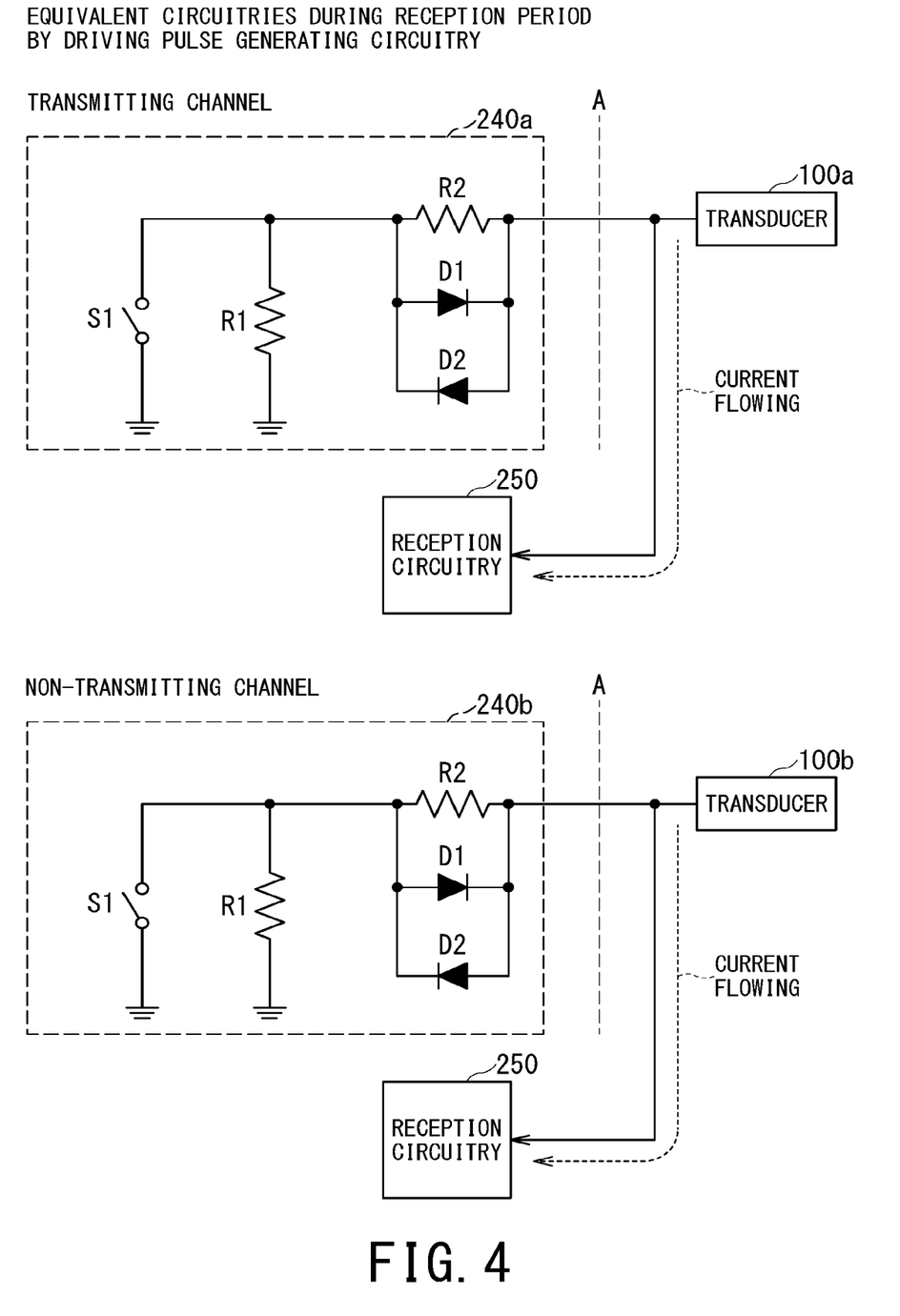
FIG. 4 is a diagram for describing equivalent circuitries during a reception period, the equivalent circuitries being included in the driving pulse generating circuitry of the ultrasound diagnostic apparatus according to the present embodiment.

Hereunder, operations for controlling the output impedance of the driving pulse generating circuitry 240 is described based on equivalent circuitries illustrated in FIGS. 3 and 4.

First, operations of transmitting channels and non-transmitting channels during a transmission period will be described.

FIG. 3 is a diagram for describing equivalent circuitries during a transmission period, the equivalent circuitries being included in the driving pulse generating circuitry 240 of the ultrasound diagnostic apparatus 1 according to the present embodiment.

FIG. 3 illustrates an adjacent transmitting channel and non-transmitting channel during a transmission period. The upper section in FIG. 3 illustrates the transmitting channel, and the lower section in FIG. 3 illustrates the non-transmitting channel.

As shown in the upper section in FIG. 3, in the transmitting channel, a transducer 100a, a driving pulse generating circuitry 240a and the reception circuitry 250 are connected. The driving pulse generating circuitry 240a includes a resistance R1, a resistance R2, and anti-parallel diodes D1 and D2 that are connected in parallel (hereunder, these two diodes may be referred to as "anti-parallel diodes D1, D2"), and a driving pulse generation source PS. One end of the resistance R2 is connected to the transducer 100a, and the other end of the resistance R2 is connected to one end of the resistance R1 and one end of the driving pulse generation source PS. The anti-parallel diodes D1, D2 are connected in parallel to the resistance R2. The other end of each of the resistance R1 and the driving pulse generation source PS is grounded.

On the other hand, unlike the transmitting channel, an equivalent circuitry during a transmission period of a driving pulse generating circuitry 240b of the non-transmitting channel illustrated in the lower section in FIG. 3 includes a switching element S1 instead of the driving pulse generation source PS. One end of the switching element S1 is connected to the resistance R2, and the other end is grounded. In the non-transmitting channel, the switching element S1 is in a closed state ("on" state) during a transmission period. Because the switching element S1 is in an on state, the output impedance of the driving pulse generating circuitry 240b can be set to a low impedance.

Note that, the output impedance of the driving pulse generating circuitry 240a is the impedance of the driving pulse generating circuitry 240a as seen from the transducer 100a side, and is the impedance when the driving pulse generating circuitry 240a is seen from a position indicated by a dashed line A in FIG. 3. When the voltage of the anti-parallel diodes D1 and D2 is less than or equal to a forward voltage (that is, during an "off" state), the output impedance of the driving pulse generating circuitry 240a is determined by the resistances R1 and R2 which constitute the driving pulse generating circuitry 240 and the open/closed state of the switching element. On the other hand, when the voltage of the anti-parallel diodes D1 and D2 exceeds the forward voltage and a current flows in the diodes D1 and D2 (that is, during an "on" state), the output impedance of the driving pulse generating circuitry 240 is determined by an extremely small resistance of the anti-parallel diodes D1 and D2 and the resistances R1 and R2 which constitute the driving pulse generating circuitry 240 and the open/closed state of the switching element. Note that the resistance R1 is not an essential component of the driving pulse generating circuitry 240. In a case where the resistance R1 is not provided, the output impedance of the driving pulse generating circuitry 240 is determined by the open/closed state of the switching element.

In the ultrasound diagnostic apparatus 1 according to the present embodiment, by setting the output impedance of the driving pulse generating circuitry 240 of a non-transmitting channel to a low impedance during a transmission period, the influence of crosstalk from the transmission is avoided. In contrast to a transmitting channel during a transmission period in which the resistance R1 is around several hundred Ω when the anti-parallel diodes D1 and D2 are in an "on" state, because the anti-parallel diodes D1 and D2 are around 10Ω in a non-transmitting channel, transmission is performed with a small output impedance of the anti-parallel diodes D1 and D2. On the other hand, in a state in which the anti-parallel diodes D1 and D2 are "off", a combined resistance of the anti-parallel diodes D1 and D2 and the resistance R2 is transmitted as the output impedance. The transducer 100a forms a transmission pulse in accordance with the driving pulse, and transmits the transmission pulse. Crosstalk to the non-transmitting channel occurs accompanying transmission from the transmitting channel. Therefore, the switching element S1 is placed in a closed state ("on" state) in a non-transmitting channel during a transmission period. As a result, in a case where the anti-parallel diodes D1 and D2 are "off", the output impedance of the driving pulse generating circuitry 240b is substantially only the resistance value of the resistance R2. For example, by setting the resistance value of the resistance R2 to about several hundred ohms, or to a value that is less than that, the output impedance of the non-transmitting channel during a transmission period can be set to a low impedance. By setting the output impedance of the driving pulse generating circuitry 240b to a low impedance in this manner, a voltage that is generated by crosstalk can be reduced.

Thus, the above-described circuitries of the driving pulse generating circuitry 240 can suppress a voltage that is generated by crosstalk. Crosstalk generally arises in a case where there is capacitive coupling or electromagnetic coupling between adjacent circuitries. When capacitive coupling arises between a transmitting channel and a non-transmitting channel, leaking in of a transmission signal occurs depending on the presence of a parasitic capacitance between the transmitting channel and non-transmitting channel. At a time of signal transmission, a voltage that is attenuated by the reactance of a parasitic capacitance in the frequency band of the transmission signal and the impedance of the non-transmitting channel arises in the non-transmitting channel. In the present embodiment, with respect to a voltage that arises in this manner, even in a case where the anti-parallel diodes D1 and D2 of the non-transmitting channel are "off", by lowering the impedance of the non-transmitting channel by turning the switching element S1 "on", the voltage that arises in the non-transmitting channel can be suppressed.

Thus, in a non-transmitting channel during a transmission period, the output impedance of the driving pulse generating circuitry 240 is set to a low impedance to suppress a voltage that is generated by crosstalk, and hence the generation of a transmission pulse from the transducer 100 can be avoided.

Next, operations of transmitting channels and non-transmitting channels during a reception period will be described. Note that, both transmitting channels and non-transmitting channels perform reception during a reception period. Accordingly, the operations are the same in both the transmitting channels and non-transmitting channels.

FIG. 4 is a diagram for describing equivalent circuitries during a reception period, the equivalent circuitries being included in the driving pulse generating circuitry 240 of the ultrasound diagnostic apparatus 1 according to the present embodiment.

FIG. 4 illustrates an adjacent transmitting channel and non-transmitting channel during a reception period. The upper section in FIG. 4 illustrates the transmitting channel, and the lower section illustrates the non-transmitting channel. As described above, both the transmitting channel and the non-transmitting channel perform signal reception during a reception period. Hence, a description of the operations in the non-transmitting channel illustrated in the lower section in FIG. 4 is omitted.

The transmitting channel illustrated in the upper section in FIG. 4 differs from the transmitting channel illustrated in the upper section in FIG. 3 in that the transmitting channel in FIG. 4 includes the switching element S1 instead of the driving pulse generation source SP. The switching element S1 is in an open state ("off" state) during a reception period. Because the switching element S1 is in an "off" state, the output impedance of the driving pulse generating circuitry 240a is determined by a combined resistance when the resistance R1 and the resistance R2 are connected in series. In this case, although as described above the resistance R2 is, for example, about several hundred ohms or a value less than that, the resistance value of the resistance R1 is set to a higher value than the resistance R2. As a result, the output impedance during a reception period is substantially the total of R1+R2, and thus exhibits a high impedance. By setting the resistance value (R1+R2) of the combined resistance so that the output impedance of the driving pulse generating circuitry 240 becomes a higher impedance than that of the reception circuitry 250, a reception signal that the transducer 100a receives can be efficiently transferred to the reception circuitry 250.

Thus, crosstalk can be avoided by setting the output impedance of the driving pulse generating circuitry 240 of a non-transmitting channel to a low impedance during a transmission period. Further, a reception signal can be efficiently transferred to the reception circuitry 250 by setting the output impedance of the driving pulse generating circuitry 240 to a high impedance during a reception period in both the transmitting channels and non-transmitting channels.

The foregoing is a description of operations using an equivalent circuitry of the driving pulse generating circuitry 240. Next, the operations are described in further detail using FIGS. 6 and 8, based on FIG. 5 that illustrates a specific circuitry example of the driving pulse generating circuitry 240.

Figure 5:
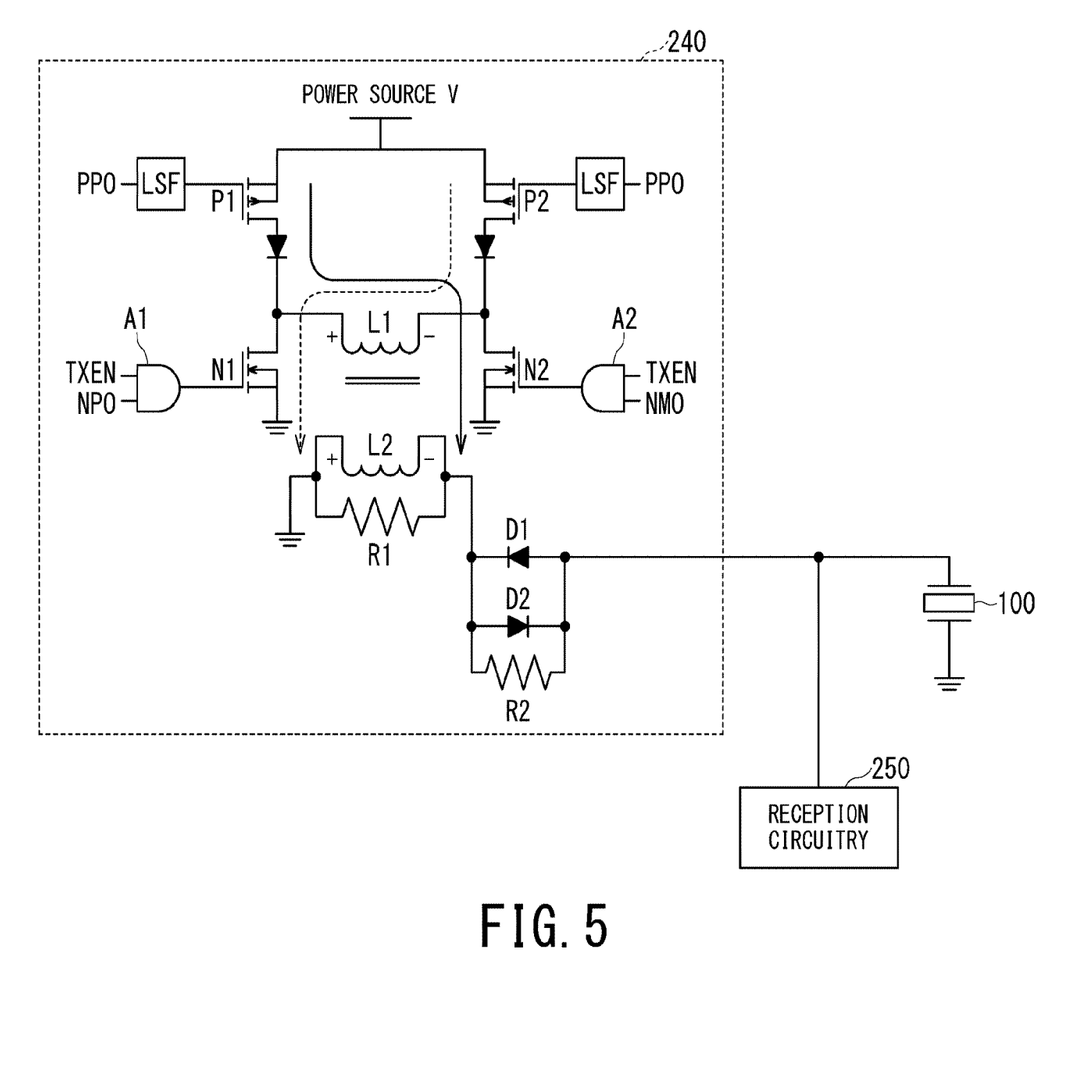
FIG. 5 is a diagram for describing a circuitry example of the driving pulse generating circuitry of the ultrasound diagnostic apparatus according to the present embodiment.

FIG. 5 is a diagram for describing a circuitry example of the driving pulse generating circuitry 240 of the ultrasound diagnostic apparatus 1 according to the present embodiment.

As shown in FIG. 5, the driving pulse generating circuitry 240 includes a power source V, field effect transistors (FET) P1, P2, N1 and N2 that function as switching elements, coils L1 and L2 constituting a transformer, AND circuitries A1 and A2, the resistances R1 and R2, and the anti-parallel diodes D1, D2.

One end (source) of the switching element P1 is connected to the power source V, and another end (drain) thereof is connected to one end of the coil L1. Likewise, one end (source) of the switching element P2 is connected to the power source V, and another end (drain) thereof is connected to one end of the coil L1. In each of the coils L1 and L2, the left end in FIG. 5 is positive and the right end is negative. One end (drain) of each of the switching elements N1 and N2 is connected to one of the two ends of the coil L1, respectively. Another end (source) of each of the switching elements N1 and N2 is grounded. Further, the respective gates of the switching elements N1 and N2 are connected to the AND circuitries A1 and A2, respectively. The coil L2 and coil L1 form a transformer and are electromagnetically coupled. The coil L2 is connected in parallel to the resistance R1. One end of the resistance R1 is connected to one end of the resistance R2. The other end of the resistance R1 is grounded. The resistance R2 is connected in parallel to the anti-parallel diodes D1, D2. The other end of the resistance R2 is connected to the transducer 100 and the reception circuitry 250.

Signals "TXEN" and "NP0" are input as control signals into the AND circuitry A1. Likewise, signals "TXEN" and "NM0" are input as control signals into the AND circuitry A2. Further, "PP0" as a control signal is input to the gate of the switching element P1, and "PM0" as a control signal is input to the gate of the switching element P2. While the switching elements N1 and N2 are N-channel FETs, the switching elements P1 and P2 are P-channel FETs. Accordingly, voltages that are input to the gates of the switching elements P1 and P2 are controlled by a level shifter (LSF) and converted to a logical level. That is, the LSF functions as an inverter, and the switching elements N1 and N2 and switching elements P1 and P2 exhibit the same behavior with respect to an inputted control signal.

Control signals that are inputted to the switching circuitries described above have a "high" and "low" status. When the relevant control signal is "high", the respective switching elements enter an on state, and when the relevant control signal is "low", the respective switching elements enter an "off" state. The AND circuitries output a "high" signal only in a case where the inputted two signals are both "high".

Note that, the signal "TXEN" is a control signal that distinguishes between a transmission period and a reception period. The signals "NP0", "NM0", "PP0", and "PM0" are control signals for forming a driving pulse.

Figure 6:
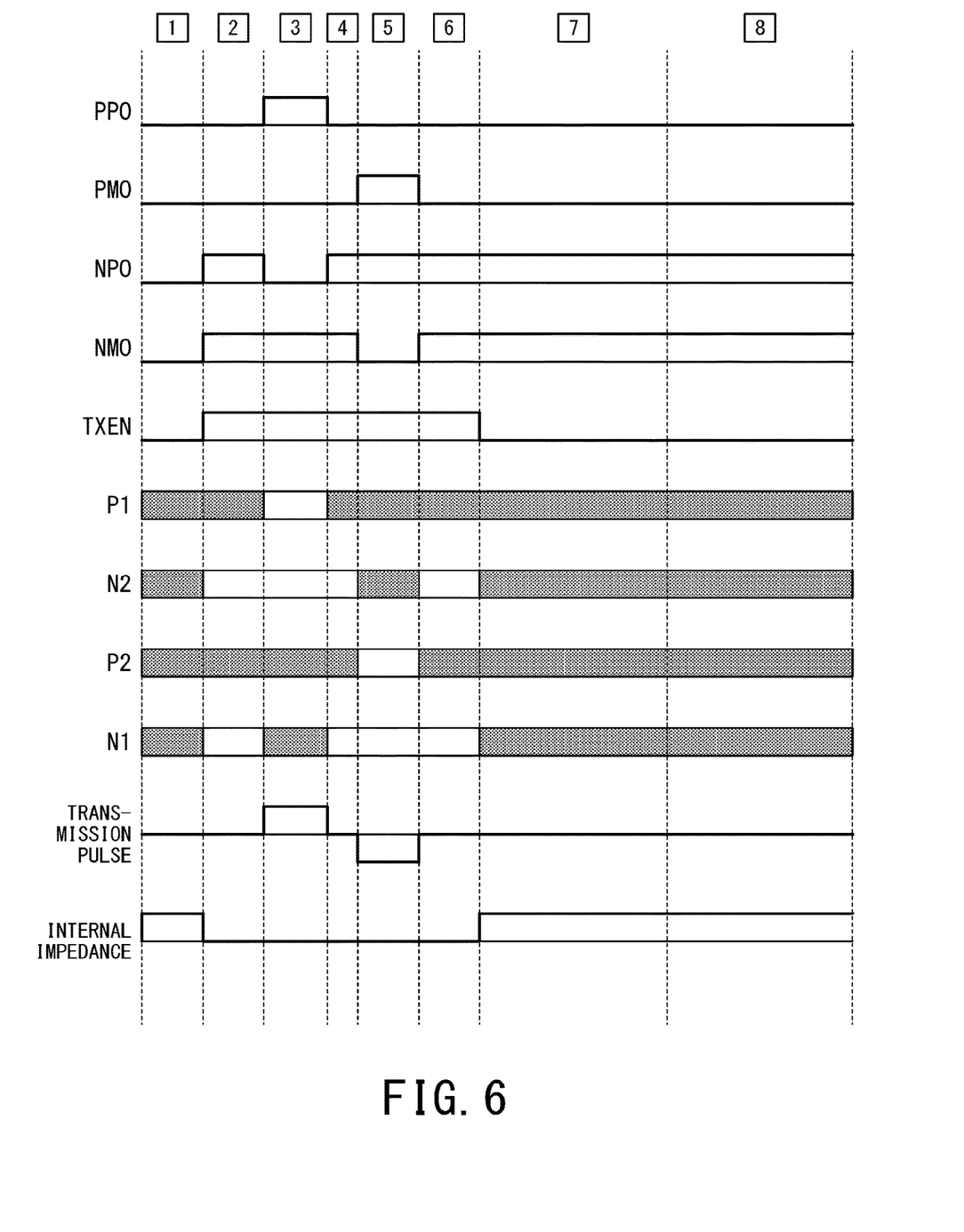
FIG. 6 is a diagram for describing operations of a transmitting channel of the ultrasound diagnostic apparatus according to the present embodiment.
Figure 7A:
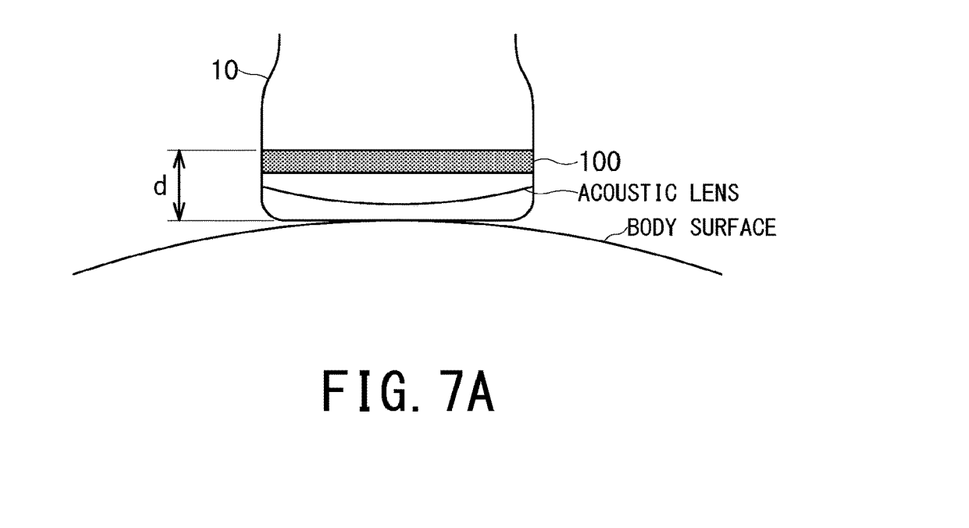
FIG. 7A is a diagram for describing the fact that an influence of switching is small in the ultrasound diagnostic apparatus according to the present embodiment.
Figure 7B:
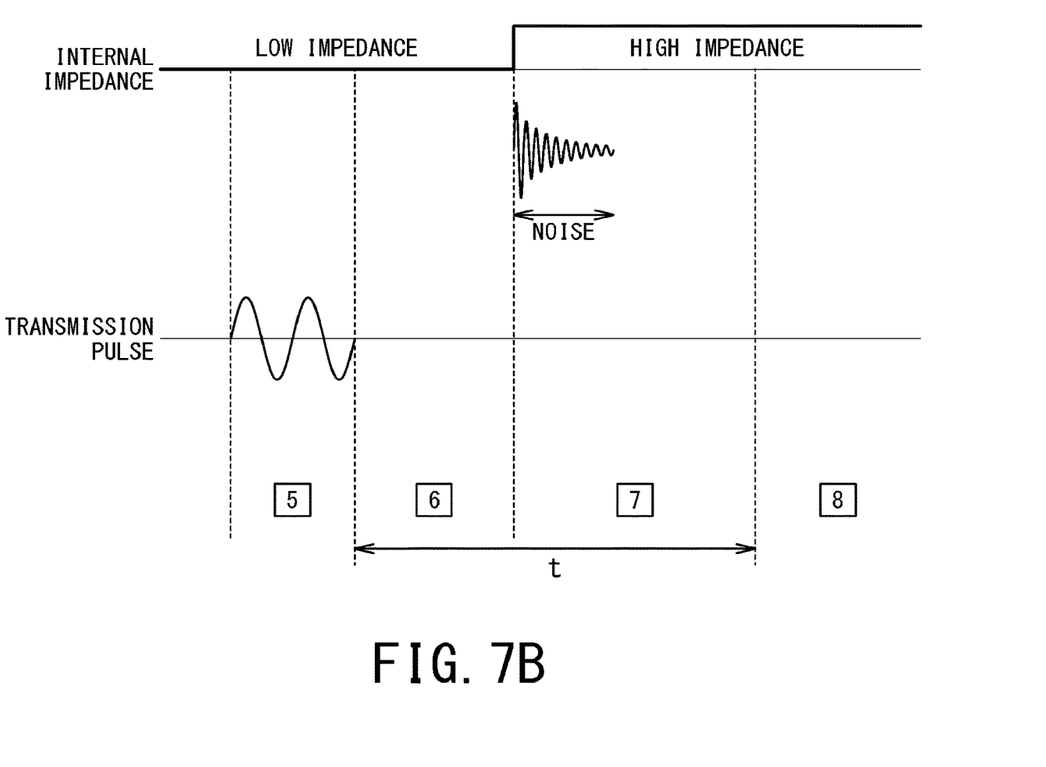
FIG. 7B is a diagram for describing the fact that an influence of switching is small in the ultrasound diagnostic apparatus according to the present embodiment.

Hereunder, operations in the circuitry example shown in FIG. 5 are described based on timing charts shown in FIGS. 6, 7A and 7B.

FIG. 6 is a diagram for describing operations of a transmitting channel of the ultrasound diagnostic apparatus 1 according to the present embodiment.

FIG. 6 illustrates a timing chart for a transmitting channel. The timing chart illustrated in FIG. 6 shows the timing chart with respect to control signals that are input to the driving pulse generating circuitry 240, operations of each switching element, a transmission pulse that is formed, and an output impedance. Note that the numbers from "1" to "8" that are shown at the upper part of FIG. 6 indicate periods in the timing chart.

In a period "1", all of the control signals are in a "low" state.

In a period "2", the three control signals "NP0", "NM0" and "TXEN" enter a "high" state.

In a period "3", "NP0" enters a "low" state and "PP0" enters a "high" state.

In a period "4", "PP0" enters a "low" state and "NP0" enters a "high" state.

In a period "5", "PM0" enters a "high" state and "NM0" enters a "low" state.

In a period "6", "PM0" enters a "low" state and "NM0" enters a "high" state.

In a period "7", "TXEN" enters a "low" state.

In the period "3", "PP0", "NM0" and "TXEN" are in a "high" state. When "PP0" is input in a "high" state to the switching element P1, because the switching element P1 accepts the control signal through the inverter, the switching element P1 turns "on". Further, when "NM0" and "TXEN" are input in a "high" state to the AND circuitry A2, and a "high" signal is input to the switching element N2, the switching element N2 turns "on". On the other hand, the switching elements P2 and N1 are in an "off" state. In FIG. 6, periods in which the respective switching elements are in an "on" state are indicated by blank (white) sections, and periods in which the respective switching elements are in an "off" state are indicated by shaded sections. As shown in FIG. 5, the left end of the coil L1 is positive and the right end is negative. In the driving pulse generating circuitry 240, because only the switching elements P1 and N2 are in an on state, a current flows from the left to the right of the coil L1 (direction of solid line arrow in FIG. 5), and a positive transmission pulse is formed.

In the period "5", "PM0", "NP0" and "TXEN" are in a "high" state. Accordingly, "PM0" is input in a "high" state to the switching element P2, and the switching element P2 turns "on". Further, when "NP0" and "TXEN" are input in a "high" state to the AND circuitry A1, and a "high" signal is input to the switching element N1, the switching element N1 turns "on". On the other hand, the switching elements P1 and N2 are in an "off" state. In the driving pulse generating circuitry 240, because only the switching elements P2 and N1 are in an "on" state, a current flows from the right to the left of the coil L1 (direction of dashed line arrow in FIG. 5), and a negative transmission pulse is formed.

As shown in the lowermost level in FIG. 6, the output impedance of the driving pulse generating circuitry 240 becomes a low impedance from the period "2" to the period "6". In contrast, the output impedance becomes a high impedance during the periods "1", "7" and "8". That is, when the two ends of the coil L1 are grounded with a low impedance or are connected to the power source V, the output impedance of the driving pulse generating circuitry 240 becomes a low impedance. Specifically, when the switching elements N1 and N2 are in an "on" state at the same time, when the switching element P1 and switching element N2 are in an "on" state at the same time, or when the switching element P2 and switching element N1 are in an "on" state at the same time, the output impedance of the driving pulse generating circuitry 240 is a low impedance.

In FIG. 6, the driving pulse generating circuitry 240 forms a transmission pulse in the periods "3" and "5", and exhibits the same state as the equivalent circuitry of the transmitting channel shown in the upper section of FIG. 3. Further, in the periods "2", "4" and "6", the switching elements N1 and N2 are in an "on" state at the same time, and exhibit the same state as the equivalent circuitry of the non-transmitting channel shown in the lower section of FIG. 3. A connecting point between the resistance R1 and the resistance R2 is equivalently grounded through the coils L1 and L2 of the transformer. Consequently, the output impedance of the driving pulse generating circuitry 240 is determined by the resistance value of the resistance R2, and exhibits a low impedance.

On the other hand, the same state as the equivalent circuitry shown in FIG. 4 is exhibited during the periods "1", "7" and "8" in which the switching elements N1 and N2 are in an "off" state. That is, the output impedance of the driving pulse generating circuitry 240 is set to a high impedance by the combined resistance of the two resistances R1 and R2.

Note that, conventionally, switching from a transmission period to a reception period is performed by switching the output impedance to a high impedance immediately after transmitting a transmission pulse. Because the output impedance becomes a high impedance immediately after transmitting a transmission pulse, an equivalent circuitry having a large time constant is formed, and switching noise that arises due to a transient response of a switching element does not attenuate for a comparatively long period and is a cause of near-field artifacts. In contrast, in the driving pulse generating circuitry 240 of the present embodiment, a configuration is adopted in which the period "6" is provided immediately after a transmission pulse is transmitted, and a low impedance is maintained in the period "6" also. As a result, switching noise (for example, switching noise that arises when the switching element N2 is switched from "on"

to "off") can be attenuated in a short time period, and the occurrence of near-field artifacts can be suppressed.

Note that, there is a possibility of switching noise arising when switching "TXEN" to "low" in order to transition to the period "7". However, because a certain time period exists until a transmission signal that is emitted into the subject is actually received, the influence of such noise can be avoided. Further, even if switching noise is generated at a switching element, because of the presence of the resistance R2, the switching noise is not directly transmitted to the reception circuitry 250 or the transducer 100, and the influence thereof can be lessened. This is because the switching noise is output after being attenuated by the input impedance of the resistance R2 and the reception circuitry 250 or the impedance of the resistance R2 and the transducer 100, and a filter effect arises at the resistance R2 and the capacitance of the reception circuitry 250 and driving pulse generating circuitry 240.

FIGS. 7A and 7B are diagrams for describing the fact that an influence of switching is small in the ultrasound diagnostic apparatus 1 according to the present embodiment.

FIG. 7A illustrates a schematic diagram of the distal end of the ultrasound probe 10. The ultrasound probe 10 includes the transducers 100 and an acoustic lens. There is a fixed distance from the body surface of the subject to the transducers 100, and a signal obtained as a result of ultrasound that is transmitted towards the subject being reflected within that distance and received as a reflected signal (a near-field reception signal) is not used as data when generating an ultrasound diagnostic image. For example, when the distance from the body surface of the subject to the transducers 100 is taken as "d", a time period in which near-field reception signals are received is taken as "t", and an acoustic velocity is taken as "v", the time period (t) in which near-field reception signals are received is represented by an equation $t=2d/v$. That is, reception signals before the time period t are near-field reception signals and are unwanted signals for generation of an ultrasound image. On the other hand, it is desirable to generate an ultrasound image based on reception signals received in a time period after the time period t (that is, reception signals that can actually be used as data). It is said that the time period t is a period of around 1 μsec, and switching noise normally attenuates and disappears in a shorter time than the aforementioned 1 μsec. Therefore, the influence of switching noise can be avoided by starting reception after an interval of a time period of around 1 μsec.

FIG. 7B illustrates operations in the periods "5" to "8" with respect to a transmitting channel. A timing at which switching noise arises due to switching of "TXEN" is the time of transitioning from period "6" to period "7". This switching noise attenuates and disappears in a shorter time period than the time period (t) in which near-field reception signals are received. Therefore, this kind of switching noise does not get mixed in with a reception signal that can actually be utilized as data.

The voltage of the driving pulse generating circuitry 240 can be reduced by temporarily placing the switching elements N1 and N2 in an on state immediately after transmission (the periods "4" and "6"), and thus a situation in which a transmission pulse does not attenuate due to a transient response after transmission and is superimposed on a reception signal can be avoided.

Further, when transitioning to the next period "7", although "TXEN" may be controlled at different timings for each channel, the wiring space can be minimized by utilizing a common "TXEN". Therefore, it is desirable to wait until transmission is completed for all transmitting channels before switching "TXEN" to "low", so that the output impedance is set to a high impedance.

Figure 8:
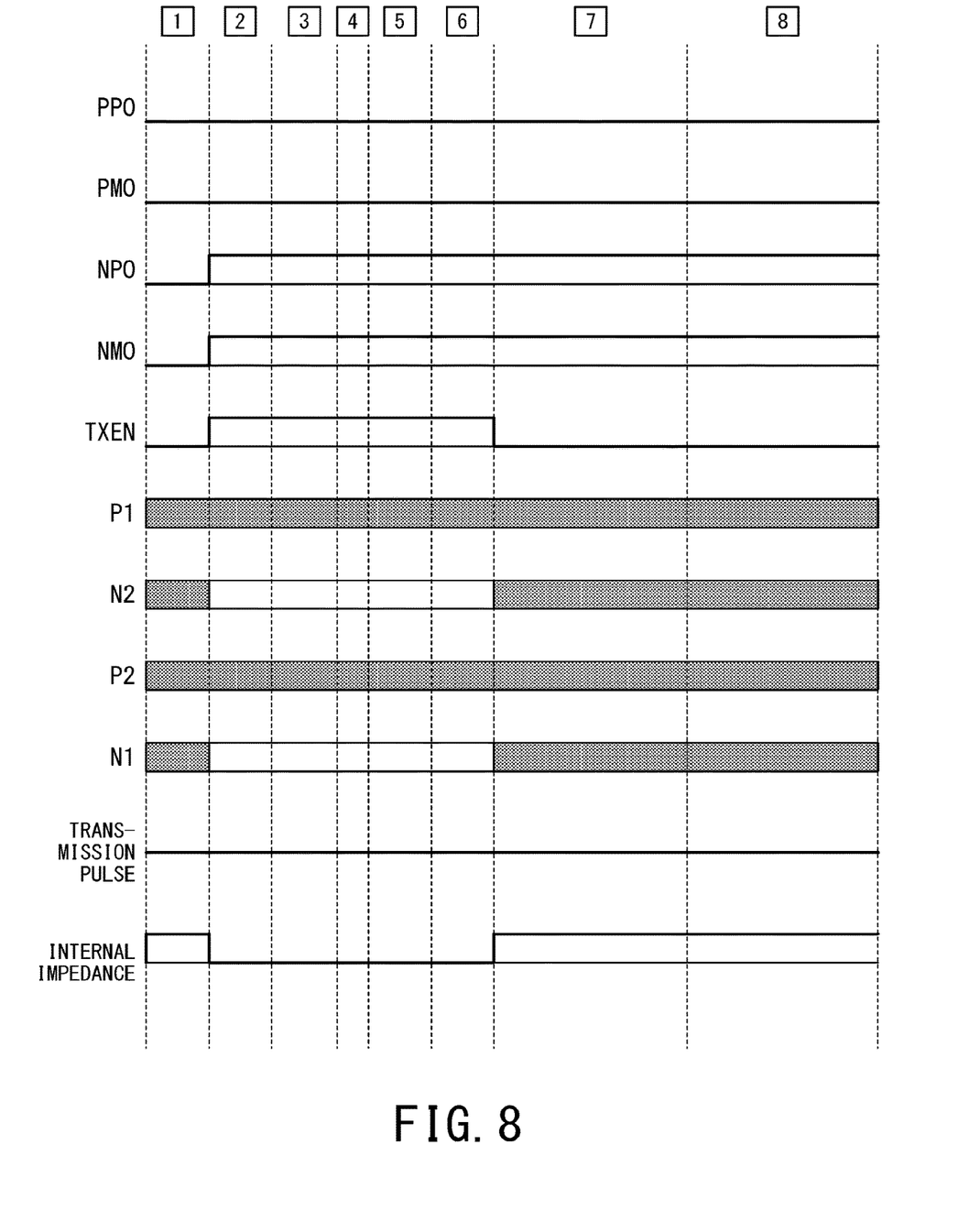
FIG. 8 is a diagram for describing operations of a non-transmitting channel of the ultrasound diagnostic apparatus according to the present embodiment.

Next, operations for a non-transmitting channel will be described. The states from the period "3" to the period "6" that are states in the process of forming a transmission pulse in the channels that transmit do not exist in the operations for a non-transmitting channel. That is, after transitioning to the low impedance state in the period "2", the operation transitions to the high impedance state in the period "7".

FIG. 8 is a diagram for describing operations of a non-transmitting channel of the ultrasound diagnostic apparatus 1 according to the present embodiment.

FIG. 8 illustrates a timing chart for a non-transmitting channel. Similarly to FIG. 6, FIG. 8 shows the timing chart with respect to control signals that are input to the driving pulse generating circuitry 240, operations of each switching element, a transmission pulse that is formed, and an output impedance. Note that, similarly to FIG. 6, the numbers from "1" to "8" that are shown at the upper part of FIG. 8 indicate periods in the timing chart.

As shown in FIG. 8, in the non-transmitting channel, unlike the transmitting channel in FIG. 6, "NP0", "NM0", and "TXEN" are in a "high" state from period "2" to period "6". When "NP0", "NM0", and "TXEN" are "high", the switching elements N1 and N2 enter an on state. As described above with respect to FIG. 6, this state is equivalent to the equivalent circuitry of the non-transmitting channel shown in the lower section in FIG. 3. That is, the output impedance of the driving pulse generating circuitry 240 is determined by the resistance value of the resistance R2, and is set to a lower impedance than the transducer 100.

On the other hand, in the periods "7" and "8", similarly to FIG. 6, the switching elements N1 and N2 enter an "off" state, and the output impedance is set to a high impedance by the resistance value of the combined resistance of the resistances R1 and R2.

The generation of a voltage in the transducer 100 can be prevented by setting the driving pulse generating circuitry 240 of the non-transmitting channel to a low impedance during a transmission period by this control and thereby causing a current generated by crosstalk to flow to a grounding point. Further, during a reception period with the reception circuitry 250, by making the impedance of the driving pulse generating circuitry 240 a high impedance, the driving pulse generating circuitry 240 does not become a load of the reception circuitry 250 and reception signals are not degraded.

Further, control of the output impedance of the driving pulse generating circuitry 240 can be realized by an extremely simple configuration, and the circuitry scale is not changed significantly when implemented within the ultrasound probe 10. There is also no kind of post-processing required with respect to a received signal, and an ultrasound image can be generated by means of existing image processing. In addition, because transmission pulses can be accurately controlled, transmission ultrasound can be emitted with the appropriate sound pressure and a favorable ultrasound image with a good S/N ratio can be acquired while maintaining the reception sensitivity.

Further, the resistance R2 that is connected in parallel with the anti-parallel diodes D1, D2 has an effect of suppressing a flow of switching noise that is generated by switching of the above described switching elements to the transducers 100 or the reception circuitry 250.

In addition, the resistance R2 also has an action that reduces distortions in a transmission pulse waveform that are caused by the anti-parallel diodes D1, D2.

Figure 9A:
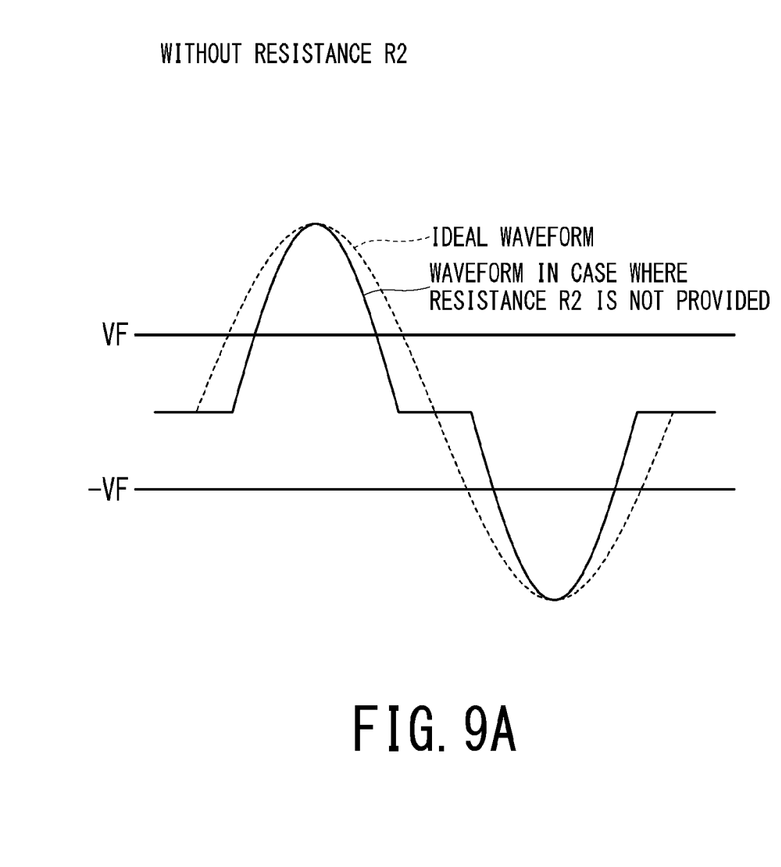
FIG. 9A is a diagram for describing distortions in a transmission waveform of the ultrasound diagnostic apparatus according to the present embodiment.
Figure 9B:
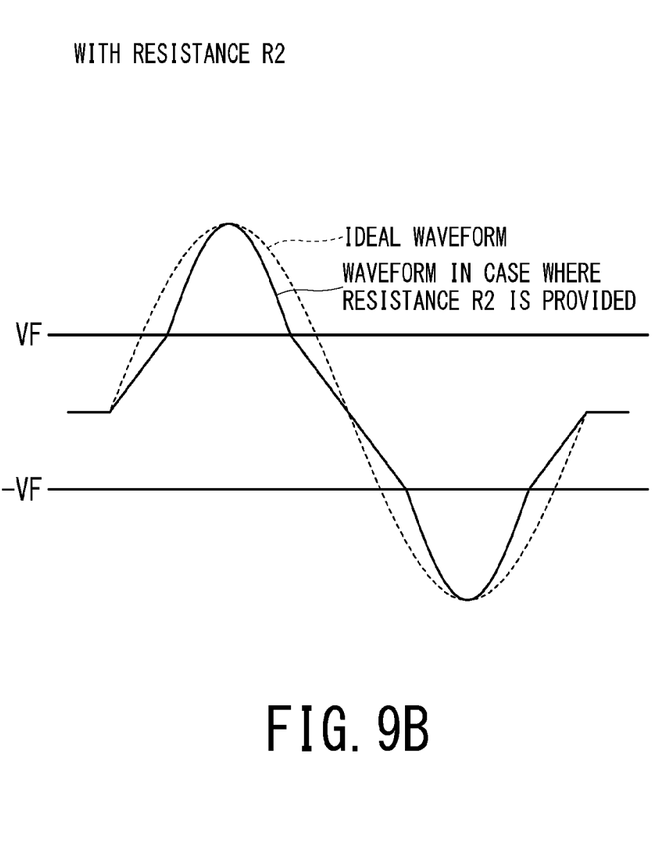
FIG. 9B is a diagram for describing distortions in a transmission waveform of the ultrasound diagnostic apparatus according to the present embodiment.

Each of FIGS. 9A and 9B is a diagram for describing distortions in a transmission waveform of the ultrasound diagnostic apparatus 1 according to the present embodiment.

FIG. 9A illustrates an example of a waveform of a transmission pulse in a case where the resistance R2 is not provided in the driving pulse generating circuitry 240. FIG. 9B illustrates an example of a waveform of a transmission pulse in a case where the resistance R2 is provided in the driving pulse generating circuitry 240. Waveforms that are indicted by dashed lines, respectively, in FIGS. 9A and 9B are ideal waveforms that it is desired to output.

In a graph illustrated by a solid line in FIG. 9A, a slope with which the transmission pulse rises and falls is steeper than the ideal waveform. This is because of a property of the diodes which is that a current first flows to the diodes D1, D2 when the voltage becomes equal to or greater than certain fixed voltages (VF and −VF). Consequently, a current does not flow when the voltage is less than a certain fixed voltage, and thus rising and falling of the waveform is abrupt and distortions arise in the waveform.

In contrast, in a graph illustrated by a solid line in FIG. 9B, a current flows even with respect to rising and falling sections of the waveform, and thus distortions are lessened. By connecting the resistance R2 in parallel to the anti-parallel diodes of the driving pulse generating circuitry 240, a current flows through the resistance R2 even in a period in which a current does not flow to the diodes, and hence the distortions in the transmission pulse waveform shown in FIG. 9A can be lessened.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An ultrasound diagnostic apparatus that controls transducers each corresponding to a channel of channels that are independent to cause the transducers to transmit and receive an ultrasound, comprising:
   a transmission control circuit configured to control each channel of the channels to be a transmission channel which transmits the ultrasound or a non-transmission channel which does not transmit the ultrasound; and
   driving pulse generating circuits each including a driving pulse generation source in which one end side of two ends is grounded, each including a resistance connected with the other end side of the driving pulse generation source and with a transducer of the transducers, and each including anti-parallel diodes connected in parallel with the resistance, the driving pulse generation source, the resistance and the transducer being connected in series, and each of the driving pulse generating circuits being configured to apply a driving pulse to the transducer,
   the transmission control circuit being configured to:
      ground the resistance through the driving pulse generation source, and thereby control so as to make an output impedance of a driving pulse generating circuit corresponding to the non-transmission channel a low impedance, and so as to make an output impedance of a driving pulse generating circuit corresponding to the transmission channel a high impedance by using a resistance value of the resistance, and
      control so as to make an output impedance of each of the driving pulse generating circuits as seen from the transducer, during a transmission period in which the ultrasound is transmitted, a lower impedance than during a reception period in which a reflected wave of the ultrasound is received, by placing anti-parallel diodes corresponding to at least the non-transmission channel in an "off" state during the transmission period and making an output impedance of each of driving pulse generating circuits corresponding to at least the non-transmission channel a resistance value of the resistance.

2. The ultrasound diagnostic apparatus according to claim 1, wherein
   the transmission control circuit is further configured to control so as to make the output impedance of each of the driving pulse generating circuits a higher impedance than an impedance in a reception circuit in all channels during the reception period.

3. The ultrasound diagnostic apparatus according to claim 1, wherein
   the transmission control circuit is configured to generate a control signal for forming the driving pulse, and a control signal that distinguishes between the transmission period and the reception period.

4. The ultrasound diagnostic apparatus according to claim 1, wherein
   the resistance, connected in parallel with the anti-parallel diodes, is configured to suppress transmission of a switching noise that is generated by switching between the low impedance and the high impedance to the transducers and a reception circuit.

5. The ultrasound diagnostic apparatus according to claim 4, wherein
   the resistance is configured to suppress distortion of a transmission pulse waveform that is generated by the anti-parallel diodes in a low voltage period.

6. The ultrasound diagnostic apparatus according to claim 1, further comprising
   an ultrasound probe including the transducers.

7. The ultrasound diagnostic apparatus according to claim 1, wherein
   the transmission control circuit is configured to control the transmission channel and the non-transmission channel in accordance with an aperture width.

8. The ultrasound diagnostic apparatus according to claim 1, wherein
   the transmission control circuit is configured to control the transmission channel and the non-transmission channel in accordance with a transmission sound pressure under a harmonic imaging.

9. The ultrasound diagnostic apparatus according to claim 1, wherein
   the transmission control circuit is configured to control so as to make the output impedance of each of the driving pulse generating circuits as seen from the transducer, during the transmission period, the lower impedance than during the reception period, by placing anti-parallel diodes corresponding to the transmission channel in an "off" state during the transmission period.

* * * * *